US009068172B2

(12) United States Patent
Paul (10) Patent No.: US 9,068,172 B2
(45) Date of Patent: Jun. 30, 2015

(54) STEP-DERIVED PEPTIDE FOR BRAIN INJURY TREATMENT

(75) Inventor: Surojit Paul, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 0 days.

(21) Appl. No.: 13/823,856

(22) PCT Filed: Sep. 15, 2011

(86) PCT No.: PCT/US2011/051827
§ 371 (c)(1),
(2), (4) Date: Mar. 15, 2013

(87) PCT Pub. No.: WO2012/037397
PCT Pub. Date: Mar. 22, 2012

(65) Prior Publication Data
US 2014/0170130 A1 Jun. 19, 2014

Related U.S. Application Data (60) Provisional application No. 61/383,208, filed on Sep. 15, 2010.

(51) Int. Cl.
| | | |
|---|---|---|
| C07K 14/47 | (2006.01) |
| C07K 19/00 | (2006.01) |
| A61K 38/17 | (2006.01) |
| A61P 25/00 | (2006.01) |
| C12N 9/16 | (2006.01) |
| A61K 38/00 | (2006.01) |

(52) U.S. Cl.
CPC . *C12N 9/16* (2013.01); *A61K 38/00* (2013.01); *C12Y 301/03048* (2013.01)

(58) Field of Classification Search
CPC ........ A61K 38/17; A61P 25/00; C07K 14/47; C07K 19/00; C12N 9/16
See application file for complete search history.

(56) References Cited

U.S. PATENT DOCUMENTS

| | | | |
|---|---|---|---|
| 6,015,834 | A | 1/2000 | Charlton et al. |
| 7,767,204 | B2 | 8/2010 | Teichberg |
| 2009/0004112 | A1 | 1/2009 | Abeliovich |
| 2009/0304661 | A1 | 12/2009 | Teichberg |

FOREIGN PATENT DOCUMENTS

| | | |
|---|---|---|
| WO | 2005/055813 | 6/2005 |
| WO | 2009099563 A2 | 8/2009 |

OTHER PUBLICATIONS

Paul et al., "NMDA-mediated activation of the tyrosine phosphatase STEP regulates the duration of ERK signaling" Nat. Neurosci. 6:34-42 (2002)—copy provided with IDS filed Mar. 22, 2013.*
Braithwaite et al., "Synaptic plasticity: one STEP at a time," Trends in Neurosci. 29:452-458 (2006).*
Mukherjee et al., "Dephosphorylation of specific sites in the kinase-specificity sequence domain leads to ubiquitin-mediated degradation of the tyrosine phosphatase STEP," Biochem. J. 440:115-215 (2011)).*
Paul et al,. "The dopamine/01 receptor mediates the phosphorylation and inactivation of the protein tyrosine phosphatase STEP via a PKA-dependent pathway" The Journal of Neuroscience, vol. 20. No . I5. pp. 5630-5638 (Aug. 1, 2000).
Paul et al., "The striatal-enriched protein tyrosine phosphatase gates long-term potentiation and fear memory in the lateral amygdala" Biological Psychiatry. vol. 61, pp. I049-1061 (2007).
International Search Report for PCT/US13/51827, mailed Apr. 9, 2012.
Boulanger et al., "Cellular and Molecular Characterization of a Brain-enriched Protein Tyrosine Phosphatase" The Journal of Neuroscience, Feb. 1995, 15(2): 1532-1544.
Tashev R et al. "A Substrate Trapping Mutant Form of Striatal-Enriched Protein Tyrosine Phosphatase Prevents Amphetamine-Induced Stereotypies and Long-Term Potentiation in the Striatum", Biological Psychiatry, Elsevier Science, New York, NY; US, vol. 65, No. 8, Apr. 15, 2009, pp. 637-645, XP026072584, ISSN: 0006-3223, DOI: 10.1016/J.Biopsych.2008.10.008.
Arundine, et al., "Molecular Mechanisms of Glutamate-Dependent Neurodegeneration in Ischemia and Traumatic Brain Injury", Cell Mol Life Science, vol. 61, 2004, 657-668.
Barone, et al., "Inhibition of p38 Mitogen-Activated Protein Kinase Provides Neuroprotection in Cerebral Focal Ischemia", Medicinal Research Reviews, vol. 21, Issue 2, 2001, 129-145.
Barone, et al., "SB 239063, a Second-Generation p38 Mitogen-Activated Protein Kinase Inhibitor, Reduces Brain Injury and Nuerological Deficits in Cerebral Focal Ischemia", The Journal of Pharmacology and Experimental Therapeutics, vol. 296, 2001, 312-321.
Braithwaite, et al., "Expression and function of striatal enriched protein tyrosine phosphatase is profoundly altered in cerebral ischemia", Eur J Neurosci, vol. 27, No. 9, 2008, 2444-2452.
Braithwaite, et al., "Regulation of NMDA receptor trafficking and function by striatal-enriched tyrosine phosphatase (STEP)", European Journal of Neuroscience, vol. 23, 2006, 2847-2856.

(Continued)

*Primary Examiner* — Julie Ha
*Assistant Examiner* — Kristina M Hellman
(74) *Attorney, Agent, or Firm* — Gonzales Patent Services; Ellen M. Gonzales (57) ABSTRACT

A novel peptide sequence that is a modified derivative of a neuron-specific tyrosine phosphatase is shown and described. Specifically, the novel peptide sequence is a modified derivative of striatal-enriched tyrosine phosphatase (STEP). The peptide sequence has been modified so as to be able to ameliorate and treat brain injury resulting from excessive glutamate release and/or oxidative stress. Examples of the types of brain injury which the presently disclosed peptide sequence is useful for treating includes acute brain injury resulting from stroke or traumatic brain injury and chronic disorders such as Huntington's chorea and schizophrenia. Furthermore, the presently described peptide sequence may further be useful in the treatment and amelioration of disorders associated with fear memory such as post-traumatic stress disorder.

19 Claims, 4 Drawing Sheets

(56) References Cited

OTHER PUBLICATIONS

Bullock, et al., "Massive Persistent Release of Excitatory Amino Acids Following Human Occlusive Stroke", Stroke, vol. 26, 1995, 2187-2189.

Bult, et al., "STEP: A family of brain-enriched PTPs. Alternative splicing produces transmembrane, cytosolic and truncated isoforms", European Journal of Cell Biology, vol. 72, 1997, 337-344.

Bult, et al., "STEP61: A Member of a Family of Brain-Enriched PTPs is Localized to the Endoplasmic Reticulum", The Journal of Neuroscience, vol. 16, No. 24, 1996, 7821-7831.

Candelario-Jalil, et al., "Wide therapeutic time window for nimesulide neuroprotection in a model of transient focal cerebral ischemia in the rat", Brain Research, vol. 1007, 2004, 98-108.

Chazot, "The NMDA receptor NR2B subunit: a valid therapeutic target for multiple CNS pathologies", Curr Med Chem., vol. 11, No. 3, 2004, 389-396.

Davalos, et al., "Duration of Glutamate Release After Acute Ischemic Stroke", Stroke, vol. 28, 1997, 708-710.

Deb, et al., "Oxidative stress induced oligomerization inhibits the activity of the non-receptor tyrosine phosphatase STEP", J Neurochem, vol. 116, No. 6, 2011, 1097-1111.

Dirnagl, et al., "Pathobiology of ischaemic stroke: an integrated view", TINS vol. 22, No. 9, 1999, 391-397.

Iadecola, et al., "Reduced susceptibility to ischemic brain injury and N-methyl-D-aspartate-mediated neurotoxicity in cyclooxygenase-2-deficient mice", Proc Natl Acad Sci, vol. 98, No. 3, 2001, 1294-1299.

Kemp, et al., "NMDA receptor pathways as drug targets", Nature Neuroscience Supplement, vol. 5, 2002, 1039-1042.

Kohr, "NMDA receptor function: subunit composition versus spatial distribution", Cell Tissue Res, vol. 326, 2006, 439-446.

Lipton, et al., "Excitatory Amino Acids as a Final Common Pathway for Neurologic Disorders", The New England Journal of Medicine, vol. 330, No. 9, 1994, 613-622.

Lipton, "Failures and Successes of NMDA Receptor Antagonists: Molecular Basis for the Use of Open-Channel Blockers like Memantine in the Treatment of Acute and Chronic Neurologic Insults", NeuroRx, vol. 1, No. 1, 2004, 101-110.

Liu, et al., "NMDA Receptor Subunits Have Differential Roles in Mediating Excitotoxic Neuronal Death Both in Vitro and in Vivo", The Journal of Neuroscience, vol. 27, No. 11, 2007, 2846-2857.

Lombroso, et al., "A Protein Tyrosine Phosphate Expressed within Dopaminoceptive Neurons of the Basal Ganglia and Related Structures", The Journal of Neuroscience, vol. 13, No. 7, 1993, 3064-3074.

Luo, et al., "The Majority of N-Methyl-D-Aspartate Receptor Complexes in Adult Rat Cerebral Cortex Contain at Least Three Different Subunits (NR1/NR2A/NR2B)", Molecular Pharmacology, vol. 51, 1997, 79-86.

Mehta, et al., "Molecular targets in cerebral ischemia for developing novel therapeutics", Brain Research Reviews, vol. 54, 2007, 34-66.

Munoz, et al., "Differential interaction of the tyrosine phosphatases PTP-SL, STEP and HePTP with the mitogen-activated protein kinases ERK1/2 and p38α is determined by a kinase specificity sequence and influenced by reducing agents", Biochem J., vol. 372, 2003, 193-201.

Nguyen, et al., "Striatal Enriched Phosphatase 61 Dephosphorylates Fyn at Phosphotyrosine 420", J. Biol. Chem., vol. 277, 2002, 24274-24279.

Nito, et al., "Role of the p38 mitogen-activated protein kinase/cytosolic Phospholipase A2 signalling pathway in blood-brain barrier disruption after focal cerebral ischemia and reperfusion", J Cereb Blood Flow Metab, vol. 28, No. 10, 2008, 1686-1696.

Paul, et al., "The Protein Tyrosine Phosphatase STEP Gates Long-term Potentiation and Fear Memory in the Lateral Amygdala", Biol Psychiatry, vol. 61, No. 9, 2007, 1049-1061.

Poddar, "Homocysteine-NMDA receptor mediated activation of extracellular-signal regulated kinase leads to neuronal cell death", J Neurochem, vol. 110, No. 3, 2009, 1095-1106.

Pulido, et al., "PTP-SL and STEP protein tyrosine phosphatases regulate the activation of the extracellular signalregulated kinases ERK1 and ERK2 by association through a kinase interaction motif", The EMBO Journal, vol. 17, No. 24, 1998, 7337-7350.

Rodrigues, et al., "Intra-Amygdala Blockade of the NR2B Subunit of the NMDA Receptor Disrupts the Acquisition But Not the Expression of Fear Conditioning", The Journal of Neuroscience, vol. 21, No. 17, 2001, 6889-6896.

Snyder, et al., "Regulation of NMDA receptor trafficking by amyloid-b", Nature Neuroscience, vol. 8, No. 8, 2005, 1051-1058.

Thomas, et al., "MAPK Cascade Signalling and Synaptic Plasticity", Nature Review, vol. 5, No. 3, 2004, 173-183.

Tovar, et al., "The Incorporation of NMDA Receptors with a Distinct Subunit Composition at Nascent Hippocampal Synapses in Vitro", The Journal of Neuroscience, vol. 19, No. 10, 1999, 4180-4188.

Tu, et al., "DAPK1 Interaction with NMDA Receptor NR2B Subunits Mediates Brain Damage in Stroke", Cell, vol. 140, No. 2, 2010, 222-234.

Walker, et al., "Amygdala infusions of an NR2B-selective or an NR2A-preferring NMDA receptor antagonist differentially influence fear conditioning and expression in the fear-potentiated startle test", Learning & Memory, Cold Spring Harbor Laboratory Press, NY 15, http://www.learnmem.org, 2008, 67-74.

Xu, et al., "Extrasynaptic NMDA Receptors Couple Preferentially to Excitotoxicity via Calpain-mediated Cleavage of STEP", J Neurosci, vol. 29, No. 29, 2009, 9330-9343.

Zhao, et al., "Roles of NMDA NR2B Subtype Receptor in Prefrontal Long-Term Potentiation and Contextual Fear Memory", Neuron, vol. 47, 2005, 859-872.

\* cited by examiner

TAT-STEP (anti-myc)

STEP-DERIVED PEPTIDE FOR BRAIN INJURY TREATMENT

CROSS-REFERENCE TO RELATED APPLICATIONS

The following application claims benefit of U.S. Provisional Application No. 61/383,208, filed Sep. 15, 2010, which is hereby incorporated by reference in its entirety.

STATEMENT REGARDING GOVERNMENT SPONSORED RESEARCH

This invention was made with Government support under 5R01NS059962-04 awarded by NINDS. The U.S. Government has certain rights in this invention.

SEQUENCE LISTING

A sequence listing is submitted with the present application. The sequence listing is submitted as a .txt file entitled 7120102_SEQ_ST25.txt and is 12 kb in size. The entire contents of the sequence listing are hereby incorporated by reference.

BACKGROUND

Brain injury resulting from ischemic insults such as stroke, post-traumatic lesions and a variety of neurological disorders frequently causes significant neuro-degeneration resulting in mild to severe impairment and even death to those suffering from these injuries. Current treatment methods are limited and are typically related to invasive surgical procedures and post-injury rehabilitative treatments rather than limiting or reversing the damage caused by the initial injury to the brain.

Various studies implicate excitotoxic glutamate receptor activation in neuro-degeneration following ischemic insults, post-traumatic lesions and a range of other neurological disorders (Lipton and Rosenberg 1994; Arundine and Tymianski 2004). In pathological conditions excessive release of the neurotransmitter glutamate leads to activation of NMDA-subtype of glutamate receptors that triggers a deleterious cascade of intracellular events including Ca2+ overload and activation of effector molecules like p38 mitogen activated protein kinase (p38 MAPK) that is known to be involved in excitotoxic cell death (Barone et al. 2001a; Barone et al. 2001b). Recent findings suggest the existence of two functionally distinct pools of NMDA receptors (NMDAR) defined by the presence of NR2A (NR2A-NMDAR) or NR2B (NR2B-NMDAR) containing subunits (Luo et al. 1997; Tovar and Westbrook 1999; Kohr 2006). NR2B-NMDARs are generally thought to be involved in triggering cell death and subsequent brain damage following an excitotoxic insult (Liu et al. 2007; Tu et al. 2010). However pharmaceutical application of NR2B-NMDAR antagonists have been unsuccessful in clinical trials, since they interfere with physiological functions of these receptors, in addition to blocking excitotoxic cascades (Rodrigues et al. 2001; Zhao et al. 2005; Walker and Davis 2008).

Accordingly, targeting components of the intracellular signaling cascades downstream of NMDAR signaling may provide novel compounds for therapeutic approaches to interventions in excitotoxicity.

The brain-enriched tyrosine phosphatase STEP (also known as STriatal Enriched Phosphatase or PTPN5) may be one such target molecule that is activated following stimulation of NMDARs and is emerging as an important regulator of neuronal survival and death. STEP is expressed specifically in neurons of the striatum, neo-cortex and hippocampus (Boulanger et al. 1995). $STEP_{61}$ and $STEP_{46}$, the two STEP isoforms (Bult et al. 1997) contain a highly conserved substrate-binding domain termed as the kinase interacting motif or KIM domain (Pulido et al. 1998). Phosphorylation of a critical serine residue within the KIM domain is mediated through dopamine/D1 receptor dependent activation of the Protein Kinase A (PKA) pathway (Paul et. al. 2000). Dephosphorylation of this residue by Ca2+ dependent phosphatase calcineurin, following glutamate/NMDA receptor stimulation, renders STEP active in terms of its ability to bind to its substrates (Paul et al. 2003). Active STEP, in turn can bind to and modulate the activity of its substrate through tyrosine dephosphorylation of a regulatory tyrosine residue. Known substrates of STEP include ERK (extracellular regulated kinase 1/2) and p38 MAPKs (Paul et al. 2007, Poddar et al., 2010, Xu et al., 2009), Src family tyrosine kinases and NMDAR subunits (Nguyen et al., 2002; Braithwaite et al., 2006), all of which are involved in neuronal survival and death.

DETAILED DESCRIPTION

According to various embodiments, the present disclosure provides a plurality of novel peptide sequences that are modified derivatives of a neuron-specific tyrosine phosphatase. Specifically, the novel peptide sequences are modified derivatives of striatal-enriched tyrosine phosphatase (STEP). In each of the peptide sequences, STEP has been modified so as to be able to ameliorate and treat brain injury resulting from glutamate toxicity, hypoxia and/or transient ischemic insult. Examples of the types of brain injury which the presently disclosed peptide sequences are useful for treating includes acute brain injury resulting from stroke and traumatic brain injury, and chronic disorders such as Huntington's chorea and schizophrenia. Furthermore, the presently described peptide sequences may further be useful in the treatment and amelioration of disorders associated with fear memory such as post-traumatic stress disorder.

Glutamate, the most common excitatory neurotransmitter in the brain, is a major target for clinical intervention in ischemic stroke. Sustained elevation of glutamate has been observed for at least 24 hours in patients with acute ischemic stroke (Bullock et al., 1995; Davalos et al., 1997). This maintained glutamate excitotoxicity is presumably related to the progression of ischemic brain damage over a period of hours to days after the primary event. The events leading up to glutamate toxicity begin as oxygen and glucose deprivation from ischemia result in the excessive release of glutamate followed by over activation of N-methyl-D-aspartate (NMDA)-subtype of glutamate receptors that constitutes about 80% of all the excitatory receptors in the brain. Glutamate-mediated NMDAR stimulation induces large increases in intracellular $Ca^{2+}$, leading to the activation of multiple signaling pathways that are involved in the propagation and maintenance of inflammatory response in the injured brain (Mehta et al., 2007). Activation of p38 MAPK signaling pathway in particular has been implicated in enhancing ischemic brain injury and has been linked to the production of cyclooxygenase-2, a key enzyme involved in inflammatory response and generation of reactive oxygen species (Nito et al., 2008; Iadecola et al., 2001, Barone et al., 2001a and b). However a significant concern in the pharmaceutical application of NMDA receptor antagonists is that they not only block its pathological effects but also interferes with physiological functions of NMDAR (Chazot et al., 2004; Dimagl et al., 1999; Kemp et al., 2002; Lipton et al., 2004) that includes excitatory synaptic transmission and plasticity. Therefore, identifying specific molecular targets that are activated following NMDAR stimulation and will interfere selectively with the pathological effects of NMDAR may provide novel compounds for the attenuation of ischemic brain damage.

STEP is an intracellular protein tyrosine phosphatase (PTP) that is exclusively expressed in the central nervous system. STEP is preferentially expressed in neurons of the basal ganglia, hippocampus, cortex and related structures (Lombroso et al. 1993, Boulanger et al. 1995). The STEP-family of PTPases includes both membrane associated ($STEP_{61}$) and cytosolic ($STEP_{46}$) variants that are formed by alternative splicing of a single gene (Bult et al. 1997). $STEP_{61}$ differs from $STEP_{46}$ by the presence of an additional 172 amino acids at its N-terminus (Bult et al. 1996). For the purposes of this disclosure, specific amino acids residues within the STEP protein are frequently referred to using the numbering from the $STEP_{46}$ variant. The 107 amino acid sequence of the STEP protein discussed herein is highly conserved between animal species with 95% sequence homology between mouse and human. (Compare SEQ IDs 1 and 2.) The present disclosure provides for a number of possible mutations of the STEP protein in order to achieve the useful peptides of the disclosed herein. Where the described mutation sites are conserved between species, it will be well understood that the various STEP-based peptides described herein may be based on or derived from the STEP proteins from a variety of species and that such peptides may or may not be derived from proteins that are endogenous to the specific species being treated and/or studied. Accordingly, the peptides disclosed herein should not be construed as being limited to the specific peptides sequences included in the sequence listing.

STEP along with two other PTPs, PTPRR and HePTP belongs to a family of PTPs that contains a highly conserved 16-amino acid substrate-binding domain termed the kinase interacting motif (KIM domain) (Pulido et al. 1998). A regulatory serine residue, ser 49 (ser 221 in $STEP_{61}$) lies in the middle of the KIM domain and dephosphorylation of this residue renders STEP active in terms of its ability to bind to its substrates. Phosphorylation of ser 49 is mediated by dopamine/D1 receptor dependent activation of the cAMP/PKA pathway (Paul et al. 2000) while dephosphorylation is mediated by glutamate/NMDA receptor induced activation of the Ca2+ dependent phosphatase, calcineurin (Paul et al. 2003).

A second conserved domain carboxy-terminal to the KIM domain is present in STEP, PTP-SL and HePTP. As described in further detail below, we have determined that this domain, termed the kinase specificity sequence (MS domain) includes two phosphorylation sites, Thr 59 (Thr 231 in $STEP_{61}$) and Ser 72 (Ser 244 in $STEP_{61}$), which are important in regulating the stability of the STEP protein.

Figure 1:
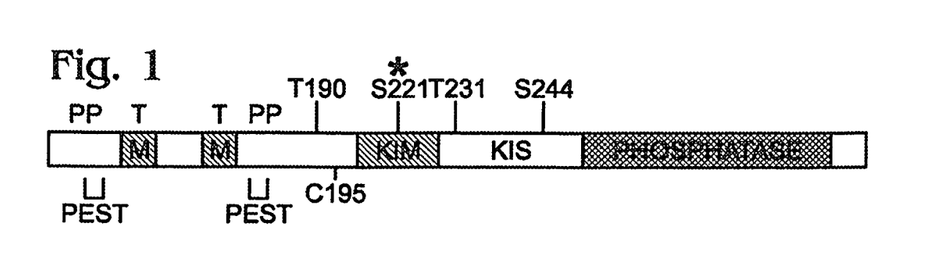
FIG. 1 is a schematic diagram of $STEP_{61}$.
Figure 2:
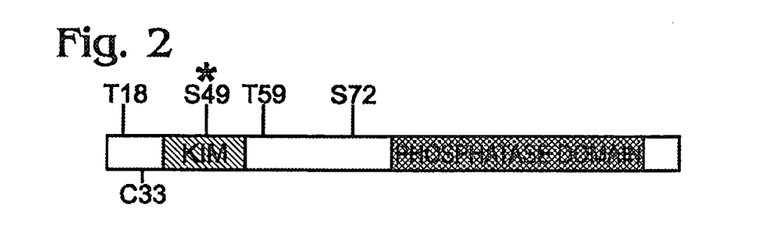
FIG. 2 is a schematic diagram of $STEP_{46}$.

FIGS. 1 and 2 are schematic diagrams of $STEP_{61}$ and $STEP_{46}$, respectively, indicating the positions of the phosphatase domain, putative proteolytic sites (PEST), transmembrane domain (TM), polyproline rich domain (PP), kinase interacting motif (KIM), kinase specificity sequence (KIS) and the above-mentioned phosphorylation sites involved in the activation and subsequent degradation of STEP. Additionally we have indicated the position of a cysteine residue (Cys 23 in $STEP_{46}$/Cys 195 in $STEP_{61}$) that has been shown to be involved in intermolecular dimerization and a threonine residue (Thr 18 in $STEP_{46}$/Thr 190 in $STEP_{61}$) that is known to be phosphorylatable by both ERK and p38 MAPKs.

In its active form STEP can modulate synaptic plasticity by regulating the activity of extracellular regulated kinase 1/2 (ERK1/2), a key protein involved in memory formation (Paul et al. 2007 and Thomas and Huganir 2004). Active STEP can also modulate NMDA receptor-dependent long term potentiation by interfering with NMDA receptor trafficking to synaptic membrane, possibly through regulation of the upstream kinase Fyn (Nguyen et al. 2002) and tyrosine dephosphorylation of NR2B-NMDA receptor subunits (Snyder et al.

2005). Several studies also indicate a role of active STEP in neuroprotection through its regulation of p38 MAPK (Poddar et al., 2010, Xu et al., 2009).

Figure 3:
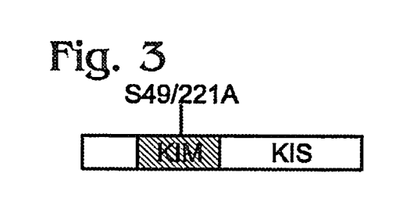
FIG. 3 is a schematic diagram of a STEP-derived peptide according to an embodiment of the present disclosure, wherein the PKA phosphorylation site * has been modified.

Because the STEP protein is known to interfere with NMDAR, a constitutively active peptide based on the STEP protein is a likely candidate for treatment, amelioration and/or prevention of ischemic brain damage. FIG. 3 is a diagram of a constitutively active STEP-derived peptide according to an embodiment of the present disclosure. The peptide contains the first 107 amino acids of STEP$_{46}$ including the KIM and KIS domains. Furthermore, as shown, the serine residue (Ser 49) which acts as a PKA phosphorylation site * has been modified. (See SEQ. ID. No. 3.) In the depicted embodiment, Ser 49 has been converted, using standard point mutation techniques, to alanine, which is non-phosphorylatable, resulting in a constitutively active peptide. Modification of the PKA phosphorylation site addresses the problem of inactivation of the STEP-derived peptide due to phosphorylation.

Additional studies, as described in Mukherjee et al. 2011, shows that the active STEP protein is more susceptible to degradation. The study highlights the role of the KIS domain in regulation of the level of active STEP. We identified two SP/TP sites (FIG. 2, Thr 59 and Ser 72) in the KIS domain whose endogenous phosphorylation is mediated primarily through the basal activity of ERK and p38 MAPKs. Dephosphorylation of these two sites selectively results in ubiquitin-mediated proteasomal degradation of the active form of STEP. These findings imply that ubiquitin-mediated proteasomal degradation of active STEP may also lead to secondary activation of p38 MAPK.

Accordingly, it may be desirable to produce an active STEP-derived peptide that remains stable and is not susceptible to ubiquitin-mediated proteasomal degradation in vivo.

Figure 4:
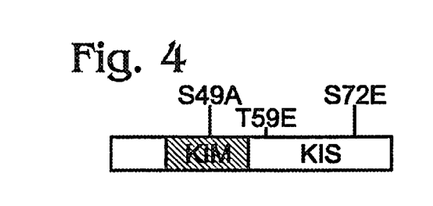
FIG. 4 is a schematic diagram of a STEP-derived peptide according to another embodiment of the present disclosure, wherein both the PKA phosphorylation site * and the KIS-domain phosphorylation sites have been modified.

FIG. 4 is a schematic illustration of a STEP-derived peptide according to an embodiment of the present disclosure, wherein Ser49 has been converted to alanine, which is non-phosphorylatable and Thr 59 and Ser 72 are converted, to glutamic acid to mimic the phosphorylatable form. (See SEQ. ID. No. 4.) However, it will be appreciated that other phopho-mimics may be used including, for example, Aspartic acid.

More recent studies as described in Deb et al., 2011, show that enzymatic activity of both STEP$_{61}$ and STEP$_{46}$ are also regulated by intermolecular dimerization. Dimerization of STEP involves intermolecular disulfide bond formation involving several cysteine residues and oxidative stress leads to increase in dimerization of STEP resulting in reduced activity. One such cysteine residue (Cys 23 in STEP$_{46}$/Cys 195 in STEP$_{61}$) that is involved in intermolecular dimerization is present in the STEP derived peptide described herein. It is possible that oxidative stress during an ischemic insult and/or reperfusion can lead to dimerization, at least in part, of the STEP derived peptide, thereby reducing its therapeutic efficacy. Accordingly, the present disclosure further provides a STEP peptide including a mutated Cys 23 residue (cysteine to alanine) (SEQ. ID. No. 5).

We have also identified another phosphorylation site in the STEP-derived peptide reported herein (Thr 18 in STEP$_{46}$/Thr 190 in STEP$_{61}$). In vitro studies show that this site is phosphorylatable by both ERK and p38 MAPKs. Based on the functional significance of phosphorylation, the present disclosure further provides a STEP peptide including a non-phosphorylatable or mimic phosphorylatable form of Thr 18 (See SEQ. ID No. 6, Thr18 mutated to Glutamic Acid and SEQ ID. No. 7, Thr18 mutated to Alanine).

SEQ ID. No. 8 provides the amino acid sequence of the human STEP Peptide including all the mutations points discussed above.

Figure 5:
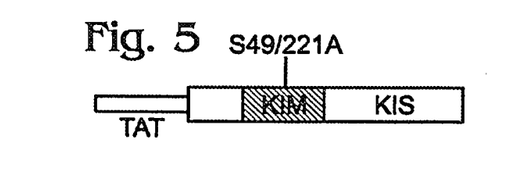
FIG. 5 is a schematic diagram of a STEP-derived peptide according to still another embodiment of the present disclosure, wherein the PKA phosphorylation site * has been modified and further including a TAT sequence at the N-terminal of the peptide.
Figure 6:
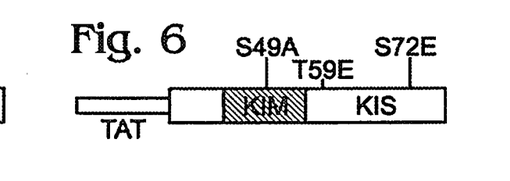
FIG. 6 is a schematic diagram of a STEP-derived peptide according to another embodiment of the present disclosure, wherein both the PKA phosphorylation site * and the KIS-domain phosphorylation sites have been modified and further including a TAT sequence at the N-terminal of the peptide.

According to some embodiments, the present disclosure provides for the prevention, treatment, or amelioration of brain injury caused by excessive glutamate release and oxidative stress. Accordingly, the present disclosure also provides STEP-derived peptides which can be delivered to the brain of a patient who is or has suffered from an incident, such as a stroke, resulting in this type of injury. FIGS. 5 and 6 are schematic illustrations of the previously described constitutively active STEP-derived peptides including a TAT sequence at the N-terminal of the peptide. In FIG. 5 only the phosphorylation site in the KIM domain has been altered. (See SEQ. ID No. 9) In FIG. 6, the phosphorylation sites in both the KIM and MS domains have been altered. (See SEQ ID. No. 10). TAT is an 11 amino acid peptide that renders peptide sequences cell permeable and enables these peptides to cross the blood brain barrier. The ability of the STEP-derived peptide to cross the blood brain barrier enables the peptide to be delivered to a patient's brain via the significantly less invasive mechanism of intravenous injection, for example via the femoral vein, rather than previous treatment mechanisms that require direct surgical access to the brain. Of course, those of skill in the art will be familiar with other suitable delivery mechanisms that could be employed including, for example, known targeted and viral-based delivery systems.

Figure 7:
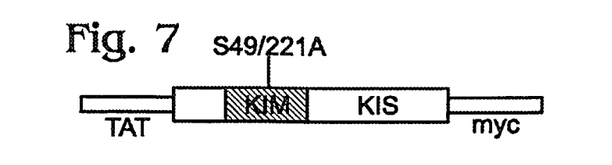
FIG. 7 is a schematic diagram of a STEP-derived peptide according to yet another embodiment of the present disclosure, wherein the PKA phosphorylation site * has been modified and further including a TAT sequence at the N-terminal of the peptide and a myc-tag at the C-terminal of the KIM domain.
Figure 8:
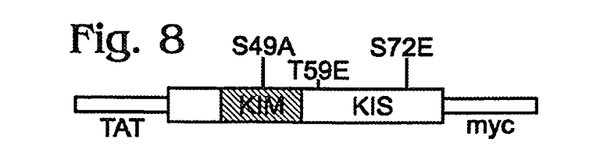
FIG. 8 is a schematic diagram of a STEP-derived peptide according to another embodiment of the present disclosure, wherein both the PKA phosphorylation site * and the MS-domain phosphorylation sites have been modified and further including a TAT sequence at the N-terminal of the peptide and a myc-tag at the C-terminal of the KIM domain.

For the purposes of experimentation, it is frequently useful to include an observable tag on the molecule being studied. Accordingly, the present disclosure further provides STEP-derived peptides including an observable tag. FIGS. 7 and 8 are schematic illustrations of the previously described constitutively active STEP-peptides including a TAT sequence at the N-terminus and wherein the C-terminus of the peptide has been modified to include a myc tag. In FIG. 7 only the phosphorylation site in the KIM domain has been altered. In FIG. 8, the phosphorylation sites in both the KIM and KIS domains have been altered. Of course, those of skill in the art will be familiar with various observable tags and mechanisms for modifying peptides to include these tags.

Using a cell culture model of glutamate toxicity we first investigated the functional significance of STEP's activation following excitotoxic NMDA receptor stimulation. As described in Paul et al., 2010, we have demonstrated that following an excitotoxic insult, NR2B-NMDA receptor mediated increases in Ca$^{2+}$ leads to dephosphorylation and subsequent activation of STEP. As described in Poddar et al., 2010, using a substrate-trapping mutant we established that p38 MAPK is a substrate of STEP and the KIM domain of STEP is involved in STEP-p38 interaction. NR2B-NMDAR mediated activation of STEP promotes cell survival by down-regulating p38 MAPK signaling pathway. However sustained NMDAR stimulation results in degradation of active STEP leading to secondary activation of p38 MAPK that triggers cell death pathways. Based on these findings we generated a constitutively active form of a STEP peptide that can bind irreversibly to p38 MAPK. It was rendered cell permeable by fusion to the protein transduction domain of the human immunodeficiency virus-type I, TAT. Transduction of the purified TAT-STEP-myc peptide in cultured neurons prior to or immediately after treatment with an excitatory dose of glutamate (100 µM, 30 min) blocked neuronal cell death as assessed by Hoechst DNA staining 24 hr later. Additional studies in an animal model of glutamate toxicity showed that the TAT-STEP peptide, when injected stereotactically into the striatum prior to glutamate, could attenuate glutamate-induced excitotoxic cell death in vivo.

In subsequent experiments we used oxygen-glucose deprivation (OGD) as an in vitro model of cerebral ischemia to evaluate the role of TAT-STEP peptide in neuroprotection following an ischemic insult. Cultured neurons were submerged in glucose free buffer in a hypoxic chamber (oxygen-glucose deprivation or OGD) for 2 hr in the presence or absence of the peptide and cell viability was tested by Hoechsy DNA staining 24 hr later. Our findings show that pre-incubation with the TAT-STEP peptide resulted in a significant reduction in OGD-induced cell death (manuscript under preparation).

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

Lipton S. A. and Rosenberg P. A. (1994) Excitatory amino acids as a final common pathway for neurologic disorders. The New England journal of medicine 330, 613-622.

Arundine M. and Tymianski M. (2004) Molecular mechanisms of glutamate-dependent neurodegeneration in ischemia and traumatic brain injury. Cell Mol Life Sci 61, 657-668.

Barone F. C., Irving E. A., Ray A. M., Lee J. C., Kassis S., Kumar S., Badger A. M., Legos J. J., Erhardt J. A., Ohlstein E. H., Hunter A. J., Harrison D. C., Philpott K., Smith B. R., Adams J. L. and Parsons A. A. (2001a) Inhibition of p38 mitogen-activated protein kinase provides neuroprotection in cerebral focal ischemia. Medicinal research reviews 21, 129-145.

Barone F. C., Irving E. A., Ray A. M., Lee J. C., Kassis S., Kumar S., Badger A. M., White R. F., McVey M. J., Legos J. J., Erhardt J. A., Nelson A. H., Ohlstein E. H., Hunter A. J., Ward K., Smith B. R., Adams J. L. and Parsons A. A. (2001b) SB 239063, a second-generation p38 mitogen-activated protein kinase inhibitor, reduces brain injury and neurological deficits in cerebral focal ischemia. The Journal of pharmacology and experimental therapeutics 296, 312-321.

Luo J., Wang Y., Yasuda R. P., Dunah A. W. and Wolfe B. B. (1997) The majority of N-methyl-D-aspartate receptor complexes in adult rat cerebral cortex contain at least three different subunits (NR1/NR2A/NR2B). Molecular pharmacology 51, 79-86.

Tovar K. R. and Westbrook G. L. (1999) The incorporation of NMDA receptors with a distinct subunit composition at nascent hippocampal synapses in vitro. J Neurosci 19, 4180-4188.

Kohr G. (2006) NMDA receptor function: subunit composition versus spatial distribution. Cell and tissue research 326, 439-446.

Liu Y., Wong T. P., Aarts M., Rooyakkers A., Liu L., Lai T. W., Wu D. C., Lu J., Tymianski M., Craig A. M. and Wang Y. T. (2007) NMDA receptor subunits have differential roles in mediating excitotoxic neuronal death both in vitro and in vivo. J Neurosci 27, 2846-2857.

Tu W., Xu X., Peng L., Zhong X., Zhang W., Soundarapandian M. M., Balel C., Wang M., Jia N., Zhang W., Lew F., Chan S. L., Chen Y. and Lu Y. (2010) DAPK1 interaction with NMDA receptor NR2B subunits mediates brain damage in stroke. Cell 140, 222-234.

Rodrigues S. M., Schafe G. E. and LeDoux J. E. (2001) Intra-amygdala blockade of the NR2B subunit of the NMDA receptor disrupts the acquisition but not the expression of fear conditioning. J Neurosci 21, 6889-6896.

Zhao M. G., Toyoda H., Lee Y. S., Wu L. J., Ko S. W., Zhang X. H., Jia Y., Shum F., Xu H., Li B. M., Kaang B. K. and Zhuo M. (2005) Roles of NMDA NR2B subtype receptor in prefrontal long-term potentiation and contextual fear memory. Neuron 47, 859-872.

Walker D. L. and Davis M. (2008) Amygdala infusions of an NR2B-selective or an NR2A-preferring NMDA receptor antagonist differentially influence fear conditioning and expression in the fear-potentiated startle test. Learning & memory (Cold Spring Harbor, N.Y. 15, 67-74.

Boulanger L. M., Lombroso P. J., Raghunathan A., During M. J., Wahle P. and Naegele J. R. (1995) Cellular and molecular characterization of a brain-enriched protein tyrosine phosphatase. J Neurosci 15, 1532-1544.

Bult A., Zhao F., Dirkx R., Jr., Raghunathan A., Solimena M. and Lombroso P. J. (1997) STEP: a family of brain-enriched PTPs. Alternative splicing produces transmembrane, cytosolic and truncated isoforms. European journal of cell biology 72, 337-344.

Pulido R., Zuniga A. and Ullrich A. (1998) PTP-SL and STEP protein tyrosine phosphatases regulate the activation of the extracellular signal-regulated kinases ERK1 and ERK2 by association through a kinase interaction motif. The EMBO journal 17, 7337-7350.

Paul S., Snyder G. L., Yokakura H., Picciotto M. R., Nairn A. C. and Lombroso P. J. (2000) The Dopamine/D1 receptor mediates the phosphorylation and inactivation of the protein tyrosine phosphatase STEP via a PKA-dependent pathway. J Neurosci 20, 5630-5638.

Paul S., Olausson P., Venkitaramani D. V., Ruchkina I., Moran T. D., Tronson N., Mills E., Hakim S., Salter M. W., Taylor J. R. and Lombroso P. J. (2007) The striatal-enriched protein tyrosine phosphatase gates long-term potentiation and fear memory in the lateral amygdala. Biological psychiatry 61, 1049-1061.

Poddar R. and Paul S. (2009) Homocysteine-NMDA receptor-mediated activation of extracellular signal-regulated kinase leads to neuronal cell death. Journal of neurochemistry 110, 1095-1106.

Xu J., Kurup P., Zhang Y., Goebel-Goody S. M., Wu P. H., Hawasli A. H., Baum M. L., Bibb J. A. and Lombroso P. J. (2009) Extrasynaptic NMDA receptors couple preferentially to excitotoxicity via calpain-mediated cleavage of STEP. J Neurosci 29, 9330-9343.

Nguyen T. H., Liu J. and Lombroso P. J. (2002) Striatal enriched phosphatase 61 dephosphorylates Fyn at phosphotyrosine 420. The Journal of biological chemistry 277, 24274-24279.

Braithwaite S. P., Xu J., Leung J., Urfer R., Nikolich K., Oksenberg D., Lombroso P. J. and Shamloo M. (2008) Expression and function of striatal enriched protein tyrosine phosphatase is profoundly altered in cerebral ischemia. The European journal of neuroscience 27, 2444-2452.

Bullock R, Zauner A, Woodward J, Young H F. Massive persistent release of excitatory amino acids following human occlusive stroke. Stroke. 1995; 26:2187-2189

Davalos A, Castillo J, Serena J, Noya M. Duration of glutamate release after acute ischemic stroke. Stroke. 1997; 28:708-710

Mehta S L, Manhas N, Raghubir R. Molecular targets in cerebral ischemia for developing novel therapeutics. Brain Res Rev. 2007; 54:34-66

Chazot P L. The nmda receptor nr2b subunit: A valid therapeutic target for multiple cns pathologies. Curr Med Chem. 2004; 11:389-396

Dirnagl U, Iadecola C, Moskowitz M A. Pathobiology of ischaemic stroke: An integrated view. Trends Neurosci. 1999; 22:391-397

Kemp J A, McKernan R M. Nmda receptor pathways as drug targets. Nat Neurosci. 2002; 5 Suppl:1039-1042

Lipton S A. Failures and successes of nmda receptor antagonists: Molecular basis for the use of open-channel blockers like memantine in the treatment of acute and chronic neurologic insults. NeuroRx. 2004; 1:101-110

Nito C, Kamada H, Endo H, Niizuma K, Myer D J, Chan P H. Role of the p38 mitogen-activated protein kinase/cytosolic phospholipase a2 signaling pathway in blood-brain barrier disruption after focal cerebral ischemia and reperfusion. J Cereb Blood Flow Metab. 2008; 28:1686-1696

Iadecola C, Niwa K, Nogawa S, Zhao X, Nagayama M, Araki E, Morham S, Ross M E. Reduced susceptibility to ischemic brain injury and n-methyl-d-aspartate-mediated neurotoxicity in cyclooxygenase-2-deficient mice. Proc Natl Acad Sci USA. 2001; 98:1294-1299.

Deb I, Poddar R, Paul S. Oxidative stress-induced oligomerization inhibits the activity of the non-receptor tyrosine phosphatase STEP61. J Neurochem. 2011; 116:1097-1111.

Braithwaite S P, Adkisson M, Leung J, Nava A, Masterson B, Urfer R, Oksenberg D, Nikolich K. Regulation of NMDA receptor trafficking and function by striatal-enriched tyrosine phosphatase (STEP). Eur J Neurosci. 2006; 23:2847-2856.

Candelario-Jalil E, González-Falcón A, García-Cabrera M, León O S, Fiebich B L. Wide therapeutic time window for nimesulide neuroprotection in a model of transient focal cerebral ischemia in the rat. Brain Res. 2004; 1007:98-108.

Lombroso, P. J., Naegele, J. R., Sharma, E., and Lerner, M. (1993) J Neurosci 13(7), 3064-3074

Bult, A., Zhao, F., Dirkx, R., Jr., Sharma, E., Lukacsi, E., Solimena, M., Naegele, J. R., and Lombroso, P. J. (1996) J Neurosci 16(24), 7821-7831

Paul, S., Nairn, A. C., Wang, P., and Lombroso, P. J. (2003) Nature neuroscience 6(1), 34-42

Thomas, G. M., and Huganir, R. L. (2004) Nature reviews 5(3), 173-183

Snyder, E. M., Nong, Y., Almeida, C. G., Paul, S., Moran, T., Choi, E. Y., Nairn, A. C., Salter, M. W., Lombroso, P. J., Gouras, G. K., and Greengard, P. (2005) Nature neuroscience 8(8), 1051-1058

Mukherjee, S.; Poddar, R.; Deb, I., Paul, S., (2011) "Dephosphorylation of Specific Sites in the KIS domain leads to Ubiquitin-Mediated Degradation of the tyrosine Phosphatase" (In preparation)

Deb, I.; Poddar, R.; Paul, S.; (2011) "Oxidative stress induced dimerization inhibits the activity of the non-receptor tyrosine phosphatase STEP61" Journal of Neurochemistry (In publication)

Experiments—Prevention, Treatment and Amelioration of Brain Damage with TAT-STP Peptide.

Using an animal model of cerebral ischemia (middle cerebral artery occlusion for 90 min to generate embolic stroke followed by reperfusion for 24 hr), we evaluated whether degradation of active STEP contributes to neuronal cell death and subsequent brain damage and if the modified STEP peptide can mitigate ischemic brain damage. At first we examined the temporal profile of STEP's activation and subsequent degradation following cerebral ischemia and reperfusion and also evaluated its correlation with p38 MAPK activation. The findings show a rapid but transient increase in phosphorylation of p38 MAPK within 15 min of ischemic insult. This was followed by a time-dependent decrease in p38 phosphorylation from 30 min, which returned to basal levels by 90 min. The ischemic insult not only led to rapid activation of p38 MAPK but also resulted in dephosphorylation and subsequent activation of STEP, which begins at 30 min and leads to complete dephosphorylation by 90 min. As a consequence, active STEP limits the duration of activation of p38 MAPK. Progressive down regulation of active STEP through degradation is evident from ~6 hours after reperfusion resulting in secondary activation of p38 MAPK. The secondary but not the primary activation of p38 MAPK pathway correlate with the expression of cyclooxygenase-2 (COX-2), a key enzyme that is linked to p38 MAPK activation and is involved in inflammatory response and reactive oxygen species generation (manuscript in preparation). Consistent with our hypothesis, the above findings indicate that STEP is a negative regulator of cell death pathways and that degradation of active STEP trigger signaling cascades that leads to ischemic brain injury.

Figure 9:
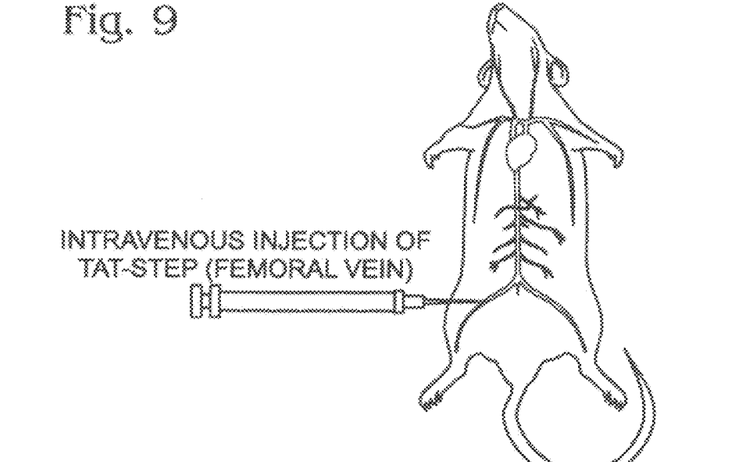
FIG. 9 is a schematic illustration showing the injection site of the TAT-STEP peptide.
Figure 10:
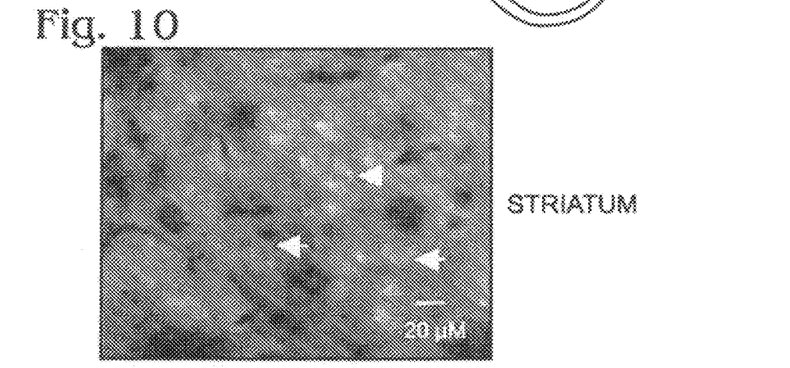
FIG. 10 shows the immunohistochemistry of coronal section of striatum with anti-myc antibody to detect exogenous TAT-STEP.
Figure 11:
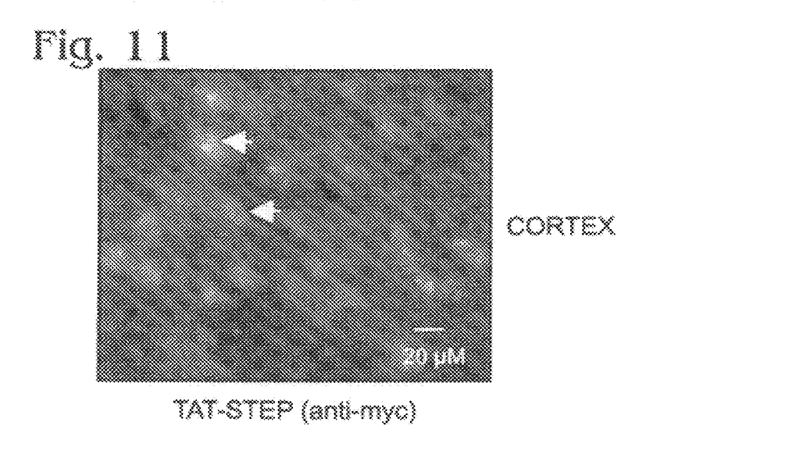
FIG. 11 shows the immunohistochemistry of cortex with anti-myc antibody to detect exogenous TAT-STEP.
Figure 12:
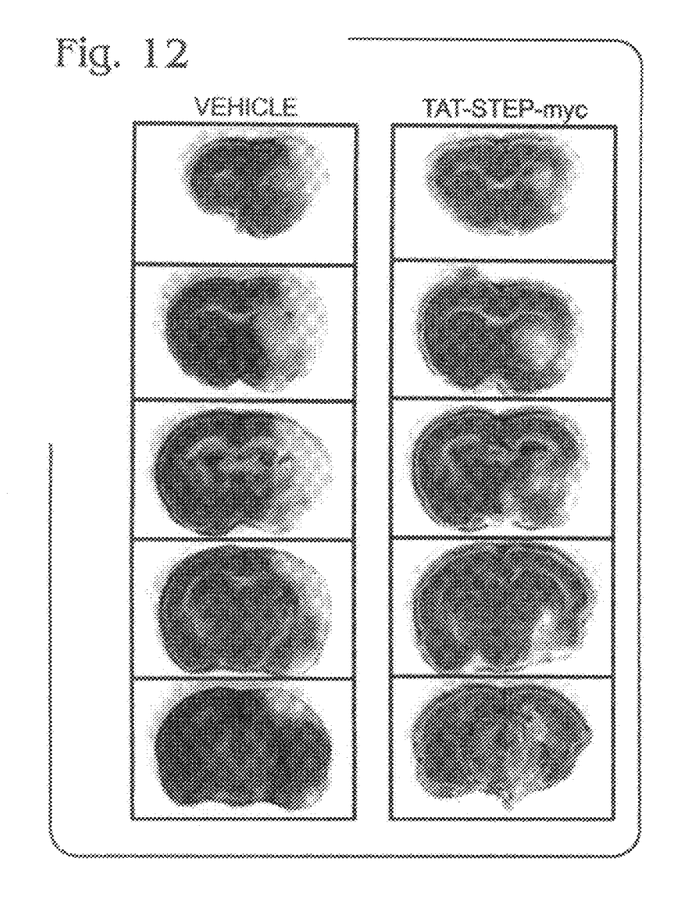
FIG. 12 shows representative TTC (triphenyltetrazolium choloride) stained sections from saline and TAT-STEP-myc treatment groups where treatment was administered immediately before an ischemic event.
Figure 13:
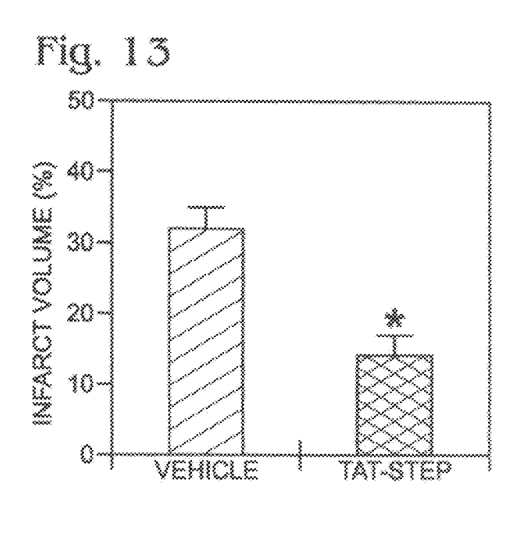
FIG. 13 is a quantitative analysis of the infarct volume. Infarct volumes are expressed as a percentage of the contralateral (control) hemisphere and the data are mean+/−SEM (p<0.01).
Figure 14:
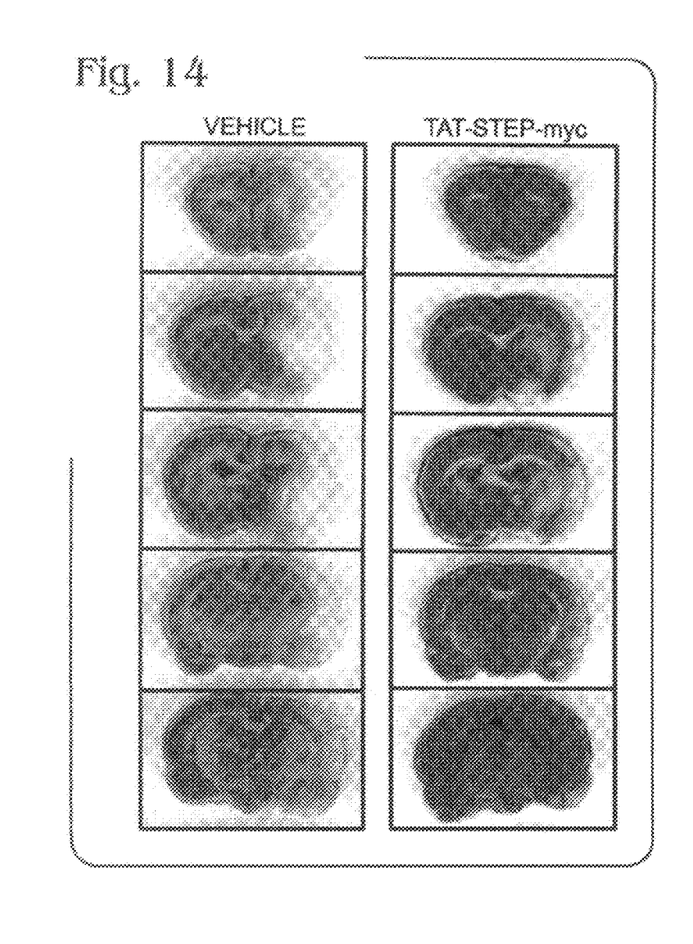
FIG. 14 shows representative TTC (triphenyltetrazolium choloride) stained sections from saline and TAT-STEP-myc treatment groups where treatment was administered 1.5 hours after an ischemic event.
Figure 15:
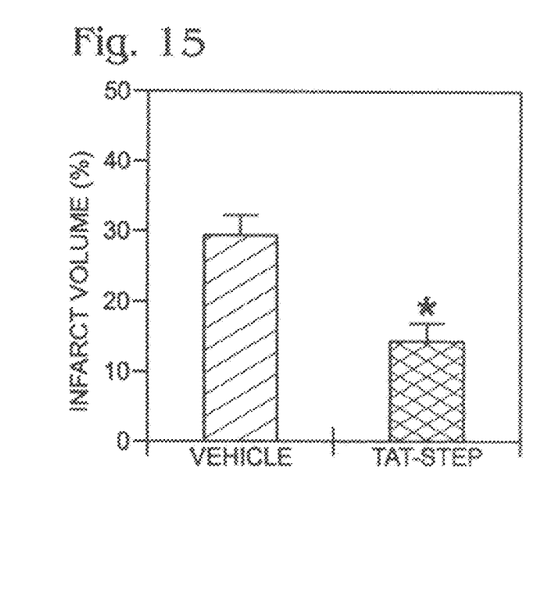
FIG. 15 is a quantitative analysis of the infarct volume. Infarct volumes are expressed as a percentage of the contralateral (control) hemisphere and the data are mean+/−SEM (p<0.01).

We next investigated whether a modified TAT-STEP peptide delivered in vivo can reduce ischemic brain damage. A major technical challenge here was to successfully deliver the peptide in the brain in a non-invasive manner. FIGS. 9-15 show that following a single intravenous injection of a TAT-STEP peptide through the femoral vein of an adult rat, the peptide was detectable both in the cortex (FIG. 10) and striatum (FIG. 11). In these experiments, Male Wistar rats received a single intravenous injection of 1 ml (1 mg/ml) of the TAT-STEP peptide of FIG. 8 through the femoral vein (FIG. 9). Detection took place 1 hour after injection.

To determine the efficacy of the peptide in attenuating ischemic brain injury, the TAT-STEP peptide of SEQ ID. No. 11 was administered intravenously immediately before or 1.5 hr after the onset of stroke. The findings demonstrate that intravenous injection of the cell-permeable STEP peptide either before or after an acute ischemic stroke can provide significant protection against ischemic brain injury. In these experiments, to generate acute ischemic stroke, male Wistar rats (260-280 gm) were subjected to middle cerebral artery occlusion (MCAO) for 90 minutes using the intraluminal suture method as described in Cadelario-Jalil et al., 2004. TAT-STEP peptide or saline was injected in the rats immediately prior to (FIG. 12-13) or 1.5 hours after (FIGS. 14-15) MCAO followed by reperfusion for 24 hr. The fact that the peptide when injected even 1.5 hr after the onset of stroke can mitigate ischemic brain injury suggests that the secondary activation of p38 MAPK following the degradation of endogenous STEP is possibly responsible for triggering intracellular death pathways. Taken together the findings further imply that the modified STEP-derived peptide may be an alternative therapeutic target, downstream of NMDAR, for intervention in diseases that involve excitotoxicity.

What is claimed is:

1. An isolated peptide comprising a kinase interacting motif (KIM) domain and a kinase specificity sequence (KIS) domain of a striatal-enriched tyrosine phosphatase (STEP) protein, wherein a serine 49 in the KIM domain is modified so as to prevent phosphorylation at that site and at least one of a threonine 59 and a serine 72 in the KIS domain is modified so as to prevent phosphorylation at that site.

2. The isolated peptide of claim 1 wherein the serine 49 residue of the KIM domain is mutated, resulting in a constitutively active peptide.

3. The isolated peptide of claim 2 wherein the serine 49 residue is replaced with an alanine residue.

4. The isolated peptide of claim 1 wherein the threonine 59 residue of the KIS domain is mutated.

5. The isolated peptide of claim 1 wherein the serine 72 residue of the KIS domain is mutated.

6. The isolated peptide of claim 1 wherein the threonine 59 residue and the serine 72 residues of the KIS domain are mutated.

7. The isolated peptide of claim 1, wherein the serine 72 residue of the KIS domain is replaced with an aspartic acid or a glutamic acid.

8. The isolated peptide of claim 1, further comprising a region configured to render the peptide cell permeable.

9. The isolated peptide of claim 8 wherein the region configured to render the peptide cell permeable is a TAT domain.

10. The isolated peptide of claim 1, further comprising a region configured to act as an observable marker.

11. The isolated peptide of claim 10 wherein the region configured to act as an observable marker is a myc region.

12. A method of treating or ameliorating ischemia comprising delivering to the patient the isolated peptide of claim 1.

13. The isolated peptide of claim 1 wherein the threonine 59 residue of the KIS domain is replaced with an aspartic acid or a glutamic acid.

14. The isolated peptide of claim 6 wherein the threonine 59 residue of the KIS domain is replaced with an aspartic acid or a glutamic acid.

15. The isolated peptide of claim 1 wherein the modification of the phosphorylation site mimics phosphorylation.

16. The isolated peptide of claim 1 wherein the isolated peptide is SEQ ID NO 4.

17. The isolated peptide of claim 1 wherein the isolated peptide is SEQ ID NO 8.

18. The isolated peptide of claim 1 wherein the isolated peptide is SEQ ID NO 10.

19. The isolated peptide of claim 1 wherein the isolated peptide is SEQ ID NO 11.

* * * * *

SEQUENCE LISTING

```
<160> NUMBER OF SEQ ID NOS: 11

<210> SEQ ID NO 1
<211> LENGTH: 107
<212> TYPE: PRT
<213> ORGANISM: Mouse

<400> SEQUENCE: 1

Met Glu Glu Lys Val Glu Asp Asp Phe Leu Asp Leu Asp Ala Val Pro
1               5                   10                  15

Glu Thr Pro Val Phe Asp Cys Val Met Asp Ile Lys Pro Glu Thr Asp
                20                  25                  30

Pro Ala Ser Leu Thr Val Lys Ser Met Gly Leu Gln Glu Arg Arg Gly
            35                  40                  45

Ser Asn Val Ser Leu Thr Leu Asp Met Cys Thr Pro Gly Cys Asn Glu
        50                  55                  60

Glu Gly Phe Gly Tyr Leu Val Ser Pro Arg Glu Glu Ser Ala His Glu
65                  70                  75                  80

Tyr Leu Leu Ser Ala Ser Arg Val Leu Arg Ala Glu Glu Leu His Glu
                85                  90                  95

Lys Ala Leu Asp Pro Phe Leu Leu Gln Ala Glu
                100                 105

<210> SEQ ID NO 2
<211> LENGTH: 107
<212> TYPE: PRT
<213> ORGANISM: Homo sapiens

<400> SEQUENCE: 2

Met Glu Glu Lys Ile Glu Asp Asp Phe Leu Asp Leu Asp Pro Val Pro
1               5                   10                  15

Glu Thr Pro Val Phe Asp Cys Val Met Asp Ile Lys Pro Glu Ala Asp
                20                  25                  30

Pro Thr Ser Leu Thr Val Lys Ser Met Gly Leu Gln Glu Arg Arg Gly
            35                  40                  45

Ser Asn Val Ser Leu Thr Leu Asp Met Cys Thr Pro Gly Cys Asn Glu
        50                  55                  60

Glu Gly Phe Gly Tyr Leu Met Ser Pro Arg Glu Glu Ser Ala Arg Glu
65                  70                  75                  80

Tyr Leu Leu Ser Ala Ser Arg Val Leu Gln Ala Glu Glu Leu His Glu
                85                  90                  95
```

Lys Ala Leu Asp Pro Phe Leu Leu Gln Ala Glu
            100                 105

<210> SEQ ID NO 3
<211> LENGTH: 107
<212> TYPE: PRT
<213> ORGANISM: Homo sapiens

<400> SEQUENCE: 3

Met Glu Glu Lys Ile Glu Asp Asp Phe Leu Asp Leu Asp Pro Val Pro
1               5                   10                  15

Glu Thr Pro Val Phe Asp Cys Val Met Asp Ile Lys Pro Glu Ala Asp
            20                  25                  30

Pro Thr Ser Leu Thr Val Lys Ser Met Gly Leu Gln Glu Arg Arg Gly
        35                  40                  45

Ala Asn Val Ser Leu Thr Leu Asp Met Cys Thr Pro Gly Cys Asn Glu
    50                  55                  60

Glu Gly Phe Gly Tyr Leu Met Ser Pro Arg Glu Glu Ser Ala Arg Glu
65                  70                  75                  80

Tyr Leu Leu Ser Ala Ser Arg Val Leu Gln Ala Glu Glu Leu His Glu
                85                  90                  95

Lys Ala Leu Asp Pro Phe Leu Leu Gln Ala Glu
            100                 105

<210> SEQ ID NO 4
<211> LENGTH: 107
<212> TYPE: PRT
<213> ORGANISM: Homo sapiens

<400> SEQUENCE: 4

Met Glu Glu Lys Ile Glu Asp Asp Phe Leu Asp Leu Asp Pro Val Pro
1               5                   10                  15

Glu Thr Pro Val Phe Asp Cys Val Met Asp Ile Lys Pro Glu Ala Asp
            20                  25                  30

Pro Thr Ser Leu Thr Val Lys Ser Met Gly Leu Gln Glu Arg Arg Gly
        35                  40                  45

Ala Asn Val Ser Leu Thr Leu Asp Met Cys Glu Pro Gly Cys Asn Glu
    50                  55                  60

Glu Gly Phe Gly Tyr Leu Met Glu Pro Arg Glu Glu Ser Ala Arg Glu
65                  70                  75                  80

Tyr Leu Leu Ser Ala Ser Arg Val Leu Gln Ala Glu Glu Leu His Glu
                85                  90                  95

Lys Ala Leu Asp Pro Phe Leu Leu Gln Ala Glu
            100                 105

<210> SEQ ID NO 5
<211> LENGTH: 107
<212> TYPE: PRT
<213> ORGANISM: Homo sapiens

<400> SEQUENCE: 5

Met Glu Glu Lys Ile Glu Asp Asp Phe Leu Asp Leu Asp Pro Val Pro
1               5                   10                  15

Glu Thr Pro Val Phe Asp Ala Val Met Asp Ile Lys Pro Glu Ala Asp
            20                  25                  30

Pro Thr Ser Leu Thr Val Lys Ser Met Gly Leu Gln Glu Arg Arg Gly
        35                  40                  45

Ser Asn Val Ser Leu Thr Leu Asp Met Cys Thr Pro Gly Cys Asn Glu

```
                    50                  55                  60
Glu Gly Phe Gly Tyr Leu Met Ser Pro Arg Glu Ser Ala Arg Glu
 65                  70                  75                  80

Tyr Leu Leu Ser Ala Ser Arg Val Leu Gln Ala Glu Leu His Glu
                 85                  90                  95

Lys Ala Leu Asp Pro Phe Leu Leu Gln Ala Glu
                100                 105

<210> SEQ ID NO 6
<211> LENGTH: 107
<212> TYPE: PRT
<213> ORGANISM: Homo sapiens

<400> SEQUENCE: 6

Met Glu Glu Lys Ile Glu Asp Asp Phe Leu Asp Leu Asp Pro Val Pro
 1               5                  10                  15

Glu Glu Pro Val Phe Asp Cys Val Met Asp Ile Lys Pro Glu Ala Asp
                20                  25                  30

Pro Thr Ser Leu Thr Val Lys Ser Met Gly Leu Gln Glu Arg Arg Gly
                35                  40                  45

Ser Asn Val Ser Leu Thr Leu Asp Met Cys Thr Pro Gly Cys Asn Glu
                50                  55                  60

Glu Gly Phe Gly Tyr Leu Met Ser Pro Arg Glu Ser Ala Arg Glu
 65                  70                  75                  80

Tyr Leu Leu Ser Ala Ser Arg Val Leu Gln Ala Glu Leu His Glu
                 85                  90                  95

Lys Ala Leu Asp Pro Phe Leu Leu Gln Ala Glu
                100                 105

<210> SEQ ID NO 7
<211> LENGTH: 107
<212> TYPE: PRT
<213> ORGANISM: Homo sapiens

<400> SEQUENCE: 7

Met Glu Glu Lys Ile Glu Asp Asp Phe Leu Asp Leu Asp Pro Val Pro
 1               5                  10                  15

Glu Ala Pro Val Phe Asp Cys Val Met Asp Ile Lys Pro Glu Ala Asp
                20                  25                  30

Pro Thr Ser Leu Thr Val Lys Ser Met Gly Leu Gln Glu Arg Arg Gly
                35                  40                  45

Ser Asn Val Ser Leu Thr Leu Asp Met Cys Thr Pro Gly Cys Asn Glu
                50                  55                  60

Glu Gly Phe Gly Tyr Leu Met Ser Pro Arg Glu Ser Ala Arg Glu
 65                  70                  75                  80

Tyr Leu Leu Ser Ala Ser Arg Val Leu Gln Ala Glu Leu His Glu
                 85                  90                  95

Lys Ala Leu Asp Pro Phe Leu Leu Gln Ala Glu
                100                 105

<210> SEQ ID NO 8
<211> LENGTH: 107
<212> TYPE: PRT
<213> ORGANISM: Homo sapiens

<400> SEQUENCE: 8

Met Glu Glu Lys Ile Glu Asp Asp Phe Leu Asp Leu Asp Pro Val Pro
 1               5                  10                  15
```

```
Glu Glu Pro Val Phe Asp Ala Val Met Asp Ile Lys Pro Glu Ala Asp
            20                  25                  30

Pro Thr Ser Leu Thr Val Lys Ser Met Gly Leu Gln Glu Arg Arg Gly
        35                  40                  45

Ala Asn Val Ser Leu Thr Leu Asp Met Cys Pro Gly Cys Asn Glu
 50                  55                  60

Glu Gly Phe Gly Tyr Leu Met Glu Pro Arg Glu Ser Ala Arg Glu
 65                  70                  75                  80

Tyr Leu Leu Ser Ala Ser Arg Val Leu Gln Ala Glu Glu Leu His Glu
                85                  90                  95

Lys Ala Leu Asp Pro Phe Leu Leu Gln Ala Glu
            100                 105
```

```
<210> SEQ ID NO 9
<211> LENGTH: 121
<212> TYPE: PRT
<213> ORGANISM: Homo sapiens

<400> SEQUENCE: 9

Met Ala Leu Tyr Gly Arg Lys Lys Arg Arg Gln Arg Arg Arg Gly Glu
 1               5                  10                  15

Glu Lys Ile Glu Asp Asp Phe Leu Asp Leu Asp Pro Val Pro Glu Thr
            20                  25                  30

Pro Val Phe Asp Cys Val Met Asp Ile Lys Pro Glu Ala Asp Pro Thr
        35                  40                  45

Ser Leu Thr Val Lys Ser Met Gly Leu Gln Glu Arg Arg Gly Ala Asn
 50                  55                  60

Val Ser Leu Thr Leu Asp Met Cys Thr Pro Gly Cys Asn Glu Glu Gly
 65                  70                  75                  80

Phe Gly Tyr Leu Met Ser Pro Arg Glu Glu Ser Ala Arg Glu Tyr Leu
                85                  90                  95

Leu Ser Ala Ser Arg Val Leu Gln Ala Glu Glu Leu His Glu Lys Ala
                100                 105                 110

Leu Asp Pro Phe Leu Leu Gln Ala Glu
        115                 120
```

```
<210> SEQ ID NO 10
<211> LENGTH: 121
<212> TYPE: PRT
<213> ORGANISM: Homo sapiens

<400> SEQUENCE: 10

Met Ala Leu Tyr Gly Arg Lys Lys Arg Arg Gln Arg Arg Arg Gly Glu
 1               5                  10                  15

Glu Lys Ile Glu Asp Asp Phe Leu Asp Leu Asp Pro Val Pro Glu Thr
            20                  25                  30

Pro Val Phe Asp Cys Val Met Asp Ile Lys Pro Glu Ala Asp Pro Thr
        35                  40                  45

Ser Leu Thr Val Lys Ser Met Gly Leu Gln Glu Arg Arg Gly Ala Asn
 50                  55                  60

Val Ser Leu Thr Leu Asp Met Cys Glu Pro Gly Cys Asn Glu Glu Gly
 65                  70                  75                  80

Phe Gly Tyr Leu Met Glu Pro Arg Glu Glu Ser Ala Arg Glu Tyr Leu
                85                  90                  95

Leu Ser Ala Ser Arg Val Leu Gln Ala Glu Glu Leu His Glu Lys Ala
                100                 105                 110
```

```
Leu Asp Pro Phe Leu Leu Gln Ala Glu
        115                 120

<210> SEQ ID NO 11
<211> LENGTH: 121
<212> TYPE: PRT
<213> ORGANISM: Mouse

<400> SEQUENCE: 11

Met Ala Leu Tyr Gly Arg Lys Lys Arg Gln Arg Arg Gly Glu
1               5                   10                  15

Glu Lys Val Glu Asp Asp Phe Leu Asp Leu Asp Ala Val Pro Glu Thr
            20                  25                  30

Pro Val Phe Asp Cys Val Met Asp Ile Lys Pro Glu Thr Asp Pro Ala
            35                  40                  45

Ser Leu Thr Val Lys Ser Met Gly Leu Gln Glu Arg Arg Gly Ala Asn
        50                  55                  60

Val Ser Leu Thr Leu Asp Met Cys Glu Pro Gly Cys Asn Glu Glu Gly
65                  70                  75                  80

Phe Gly Tyr Leu Val Glu Pro Arg Glu Glu Ser Ala His Glu Tyr Leu
                85                  90                  95

Leu Ser Ala Ser Arg Val Leu Arg Ala Glu Glu Leu His Glu Lys Ala
            100                 105                 110

Leu Asp Pro Phe Leu Leu Gln Ala Glu
        115                 120
```